(12) United States Patent
Farrell

(10) Patent No.: US 11,788,968 B2
(45) Date of Patent: *Oct. 17, 2023

(54) LATERAL FLOW ASSAY READER BASED ON HUMAN PERCEPTION AND METHOD RELATING THERETO

(71) Applicant: IDEXX Laboratories, Inc., Westbrook, ME (US)

(72) Inventor: Robert P. Farrell, Gray, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 549 days.

This patent is subject to a terminal disclaimer.

(21) Appl. No.: 17/070,868

(22) Filed: Oct. 14, 2020

(65) Prior Publication Data

US 2021/0025828 A1    Jan. 28, 2021

Related U.S. Application Data

(62) Division of application No. 15/794,998, filed on Oct. 26, 2017, now Pat. No. 10,852,242.

(Continued)

(51) Int. Cl.
*G01N 21/78* (2006.01)
*G01N 33/543* (2006.01)
(Continued)

(52) U.S. Cl.
CPC ....... *G01N 21/78* (2013.01); *G01N 33/48785* (2013.01); *G01N 33/48792* (2013.01);
(Continued)

(58) Field of Classification Search
CPC ............. G01N 21/78; G01N 33/48785; G01N 33/48792; G01N 33/54373;
(Continued)

(56) References Cited

U.S. PATENT DOCUMENTS

| | | | |
|---|---|---|---|
| 4,943,522 A | 7/1990 | Eisinger et al. | 435/7.25 |
| 5,726,010 A | 3/1998 | Clark | 435/5 |

(Continued)

FOREIGN PATENT DOCUMENTS

| | | | |
|---|---|---|---|
| CN | 102099678 A | 6/2011 | G01N 33/487 |
| CN | 102323215 A | 1/2012 | G01N 21/01 |

OTHER PUBLICATIONS

An Office Action (in Chinese) and an English translation thereof, dated Feb. 2, 2023, issued by the China National Intellectual Property Administration for Applicant's related Chinese Patent Application No. 201780074338.3, filed May 30, 2019 (PCT international filing date Oct. 26, 2017).

(Continued)

*Primary Examiner* — Dennis White
(74) *Attorney, Agent, or Firm* — Bodner & O'Rourke, LLP; Gerald T. Bodner; Christian P. Bodner

(57) ABSTRACT

An instrument for reading a lateral flow assay device by detecting color changes based on human perception includes an optics module having a camera, a signal processor, a storage memory and a comparator circuit. The storage memory has stored therein a dataset of sample readings of reference assay devices similar in structure and function to that of the lateral flow assay device. The sample readings are based on human visual perceptions of colorimetric changes in the detection zones of the reference assay devices. The comparator circuit compares the measured colorimetric data relating to the assay device read by the instrument with the stored database of sample readings based on human visual perceptions of the colorimetric changes of the reference assay devices, and generates a comparison signal which is provided to the signal processor. The signal processor generates a determination signal indicative of the presence, absence or quantity of an analyte.

50 Claims, 4 Drawing Sheets

Related U.S. Application Data

(60) Provisional application No. 62/428,174, filed on Nov. 30, 2016.

(51) Int. Cl.
    *G01N 33/487*      (2006.01)
    *G08B 5/36*      (2006.01)
    *G01N 21/84*      (2006.01)

(52) U.S. Cl.
    CPC . *G01N 33/54373* (2013.01); *G01N 33/54388* (2021.08); *G08B 5/36* (2013.01); *G01N 21/8483* (2013.01)

(58) Field of Classification Search
    CPC ......... G01N 33/54388; G01N 21/8483; G01N 33/558; G08B 5/36
    See application file for complete search history.

(56) References Cited

U.S. PATENT DOCUMENTS

| | | | |
|---|---|---|---|
| 7,940,992 B2 | 5/2011 | Johnson et al. | 382/254 |
| 8,367,013 B2 | 2/2013 | Kaylor et al. | 422/403 |
| 8,606,528 B2 | 12/2013 | Sharrock | 702/19 |
| 9,097,665 B2 | 8/2015 | Wang et al. | |
| 2005/0221505 A1 | 10/2005 | Petruno et al. | 436/524 |
| 2009/0180927 A1 | 7/2009 | Petruno et al. | 422/400 |
| 2013/0244339 A1* | 9/2013 | Ehrenkranz | G01N 33/558 436/501 |
| 2014/0001058 A1 | 1/2014 | Ghaffari et al. | 205/792 |
| 2015/0004594 A1* | 1/2015 | Sibbett | G01N 33/56988 435/287.7 |
| 2015/0160245 A1 | 6/2015 | Lieberman et al. | 506/12 |

OTHER PUBLICATIONS

An Examination Report, dated Feb. 13, 2023, issued by the Australian Patent Office for Applicant's related Australian Patent Application No. 2017366779, filed Apr. 16, 2019 (PCT international filing date Oct. 26, 2017).
"*Comparison of a new immunochromatographic test to enzyme-linked immunosorbent assay for rapid detection of immunoglobulin M antibodies to hepatitis E virus in human sera*", Chen, et al., Clinical and Diagnostic Laboratory Immunology, May 2005. vol. 12, No. 5. p. 593-598. Text available at: https://www.ncbi.nlm.nih.gov/pmc/articles/PMC1112076/ (last accessed on Sep. 28, 2022) (copy not enclosed).
A Search Report (in Chinese) and an English translation thereof, dated Jun. 10, 2022, issued by the China National Intellectual Property Administration for Applicant's related Chinese Patent Application No. 201780074338.3, filed May 30, 2019 (PCT international filing date Oct. 26, 2017).
An Office Action (in Chinese) and an English translation thereof, dated Jun. 17, 2022, issued by the China National Intellectual Property Administration for Applicant's related Chinese Patent Application No. 201780074338.3, filed May 30, 2019 (PCT international filing date Oct. 26, 2017).
An Examination Report, dated Aug. 9, 2022, issued by the Australian Patent Office for Applicant's related Australian Patent Application No. 2017366779, filed Apr. 16, 2019 (PCT international filing date Oct. 26, 2017).
A Communication Pursuant to Rule 62 EPC, dated Sep. 2, 2022, issued by the European Patent Office in Applicant's related European Patent Application No. EP22176125.7, filed on May 30, 2022 (PCT international filing date Oct. 26, 2017).
A Supplemental (Extended) European Search Report (Sep. 2, 2022—mailed with the Communication Pursuant to Rule 62 EPC), issued by the European Patent Office in Applicant's related European Patent Application No. EP22176125.7, filed on May 30, 2022 (PCT international filing date Oct. 26, 2017).
A Supplemental European Search Opinion (Sep. 2, 2022—mailed with the Communication Pursuant to Rule 62 EPC), issued by the European Patent Office in Applicant's related European Patent Application No. EP22176125.7, filed on May 30, 2022 (PCT international filing date Oct. 26, 2017).
IDEXX Laboratories, Inc., "*SNAP Pro Analyzer Operator's Guide*", 2017.
"Comparison of a New Immunochromatographic Test to Enzyme-Linked Immunosorbent Assay for Rapid Detection of Immunoglobulin M Antibodies to Hepatitis E Virus in Human Sera" (Chen, Hy et al.) Clinical and Diagnostic Laboratory Immunology, May 2005. vol. 12, No. 5. p. 594, col. 2, paragraphs 6-7; p. 596, col. 2, paragraph 2; p. 597, col. 1, paragraph 2. Text available at: https://www.ncbi.nlm.nih.gov/pmc/articles/PMC1112076/ (last accessed on Feb. 8, 2018) (copy not enclosed).
The Notification Concerning Transmittal of International Preliminary Report on Patentability (Chapter I of the Patent Cooperation Treaty), dated Jun. 13, 2019, which was issued by the International Bureau of WIPO in Applicant's related international PCT application having Serial No. PCT/US2017/058590, filed on Oct. 26, 2017.
The International Preliminary Report on Patentability (Chapter I of the Patent Cooperation Treaty), dated Jun. 4, 2019, which was issued by the International Bureau of WIPO in Applicant's related international PCT application having Serial No. PCT/US2017/058590, filed on Oct. 26, 2017.
The Written Opinion of the International Searching Authority, dated Jan. 9, 2018, which was issued by the International Bureau of WIPO in Applicant's related international PCT application having Serial No. PCT/US2017/058590, filed on Oct. 26, 2017.
The International Search Report, dated Jan. 9, 2018, which was issued by the International Bureau of WIPO in Applicant's related international PCT application having Serial No. PCT/US2017/058590, filed on Oct. 26, 2017.
A Communication Pursuant to Rule 62 EPC, dated Jun. 18, 2020, issued by the European Patent Office in Applicant's corresponding European Patent Application No. 17876864.4, filed on Jun. 28, 2019.
A Supplementary European Search Report, dated Jun. 3, 2020, issued by the European Patent Office in Applicant's corresponding European Patent Application No. 17876864.4, filed on Jun. 28, 2019.
A Supplemental European Search Opinion (Jun. 18, 2020—mailed with the Communication Pursuant to Rule 62 EPC), issued by the European Patent Office in Applicant's corresponding European Patent Application No. 17876864.4, filed on Jun. 28, 2019.

\* cited by examiner

LATERAL FLOW ASSAY READER BASED ON HUMAN PERCEPTION AND METHOD RELATING THERETO

CROSS-REFERENCE TO RELATED APPLICATIONS

This application is a divisional of U.S. patent application Ser. No. 15/794,998, filed on Oct. 26, 2017, and entitled "Lateral Flow Assay Reader Based On Human Perception And Method Relating Thereto", which claims the benefit of priority under 35 U.S.C. 119 and/or 35 U.S.C. 120 to U.S. Provisional Application Ser. No. 62/428,174, filed on Nov. 30, 2016, and entitled "Lateral Flow Assay Reader Based on Human Perception and Method Relating Thereto", the disclosure of each of which is incorporated herein by reference and on which priority is hereby claimed.

BACKGROUND OF THE INVENTION

Field of the Invention

The present invention generally relates to devices and methods for determining the presence, absence or quantity of an analyte in a liquid sample, and more specifically relates to a reader used to detect color changes in a lateral flow assay device and methods relating thereto.

Description of the Prior Art

Lateral flow assay devices 2 are well known in the art and are used extensively in the human medical and veterinary fields for testing a blood sample (i.e., whole blood, plasma or serum) or other bodily fluid (e.g. urine, saliva, milk etc.) for the presence, absence or quantity of a one or more target analytes. Target analytes can include, for example, antibodies, antigens, hormones, small molecules, drug residues and the like. When testing for antibodies or antigens, the presence of such markers is typically an indication of an infectious disease in the patient whose blood is being tested. One example of such a lateral flow assay device 2 is disclosed in U.S. Pat. No. 4,943,522, which issued to Robert W. Eisinger, et al. Another example of a lateral flow assay device 2, structured to effect a bi-directional capillary flow of a sample, is disclosed in U.S. Pat. No. 5,726,010, which issued to Scott M. Clark, the latter patented device being manufactured or distributed by IDEXX Laboratories, Inc. of Westbrook, Me. under the trademark SNAP®. Other examples of lateral flow assays, such as those that use colloidal gold for visual indication of the presence, absence or quantity of a target analyte, are well known and documented in the prior art. The disclosure of each of the aforementioned patents is incorporated herein by reference.

Many such lateral flow assay devices 2 exhibit a human perceptible colorimetric change in an exposed viewing or read area of the device 2 as an indication of the presence, absence, or quantity of an analyte in the blood sample. In the SNAP® device, a wash buffer and substrate solution are used to enhance the visible perception of color changes in the read area of the device. The wash solution removes any unbound components, sample debris and unreacted conjugate reagent from the flow matrix of the device 2, leaving a substantially clean, white background in the read area of the device 2. The substrate solution causes an enzymatic reaction which results in a distinct blue-colored dot, or dots, in the read area of the device 2 that are easy to observe against the background of the white-colored matrix. Lateral flow devices that utilize colloidal gold as a marker typically have a reddish/brown color when the particles accumulate at the test and/or control line.

FIG. 1 of the drawings is a top view of a portion of a SNAP® 4Dx® Plus lateral flow assay device 2 used for screening dogs for six vector-borne diseases. In the read area 4 of the device 2, a blue dot 6 appearing in the upper section indicates the presence of *A. phagocytophilum/A. platys* Ab in the sample being tested. The blue dot 8 on the right side of the read area 4 (when the device 2 is viewed from the front) indicates the presence of Heartworm Ag in the sample. A blue dot 10 in the lower center portion of the read area 4 of the device 2 indicates the presence of Lyme disease Ab, and a blue dot 12 on the left side of the read area 4 (when the device 2 is viewed from the front) indicates the presence of *E. canis/E. ewingii* Ab. In the upper left corner of the read area 4 of the device 2, there is located a positive control spot 14 which will turn blue if the device 2 is working properly.

There also exists instruments which read the lateral flow assay devices 2 and render an evaluation of the tests being performed, rather than having a human visually determine from the indicator or detection dots 6, 8, 10, 12 whether the test results are positive or negative. For example, the SNAP® Reader analyzer, manufactured and distributed by IDEXX Laboratories, Inc., is an image-analysis instrument which includes a digital camera. The analyzer stores and processes images of SNAP® tests according to the protocol of the specific, individual SNAP® tests designed for use with the analyzer. The SNAP® Reader analyzer then uses custom software to evaluate the results of the tests being run and reports the results. The analyzer takes digital pictures as test results are developing, and the software of the analyzer uses algorithms specific to the test to calculate the test results from these digital images. Other analyzers exist for reading lateral flow devices based on colloidal gold technology, such as: DCN Technologies, Carlsbad, Calif.; and the ESE-Quant™ lateral flow reader from Qiegen NV, Venlow, Netherlands.

Although prior art assay readers provide a quick and easy, and highly reliable, indication of the presence, absence or quantity of an analyte, in practice, there may be situations when a result may be difficult to discern. For example, with respect to device 2, the blue detection dot or dots 6, 8, 10, 12 may not be fully formed; that is, they may be crescent-shaped, rather than completely circular. Or, the dots 6, 8, 10, 12 may be intermittently colored, for example, exhibiting blue disconnected speckles. There are times when the detection dots 6, 8, 10, 12 may be only lightly colored. Similar situations occur with colloidal gold lateral flow devices. The prior art analyzer's software will apply algorithmic rules to the digital images taken by the camera of the read area which are analyzed, and make determinations as to whether the blood sample tested contains a target analyte, or whether the results are indeterminate and new tests need to be performed. The deterministic rules applied by the analyzer's software in the prior art are generally highly accurate, but are not based on human perception, to which the present invention relates.

OBJECTS AND SUMMARY OF THE INVENTION

It is an object of the present invention to provide an instrument for reading a lateral flow assay device based on human visual perceptions of colorimetric changes in the device.

It is another object of the present invention to provide a method for reading a lateral flow assay device by detecting color changes thereto based on human perception.

It is yet a further object of the present invention to provide a method and instrument for reading a lateral flow assay device which includes a detection zone in which a visually perceptible colorimetric change may occur, the instrument and method comparing images of the detection zone of the assay device against sample readings of human visual perceptions of colorimetric changes of reference assay devices in a stored database to determine whether the assay device detects the presence, absence or quantity of an analyte in a tested fluid sample.

In accordance with one form of the present invention, an instrument for reading a lateral flow assay device is provided. The lateral flow assay device performs an assay to determine the presence, absence or quantity of an analyte in a fluid sample. The assay device is placed in optical proximity to the instrument, and further has a sample deposit zone on which the fluid sample to be tested is placed. The assay device further has a detection zone in which a visually perceptible colorimetric change may occur when the assay device detects the presence, absence or quantity of an analyte in the fluid sample.

The instrument of the present invention includes an optics module. The optics module has at least one camera which is positioned on the instrument to view the detection zone of the assay device placed in optical proximity to the instrument. The at least one camera generates an output signal which is representative of an image of the detection zone of the assay device and which is indicative of a colorimetric change in the detection zone of the assay device.

The instrument of the present invention further includes a signal processor in electrical communication with the optics module. The signal processor receives the output signal from the at least one camera, and converts the signal into measured colorimetric data.

The instrument of the present invention also includes a storage memory that is in electrical communication with the signal processor. The storage memory has stored therein a dataset of sample readings of reference assay devices similar in structure and function to that of the assay device read by the instrument. These sample readings are based on human visual perceptions of colorimetric changes in the detection zones of the reference assay devices.

A comparator circuit, forming part of the instrument of the present invention, is in electrical communication with the signal processor. The comparator circuit compares the measured colorimetric data relating to the assay device read by the instrument with the stored dataset of sample readings based on human visual perceptions of the colorimetric changes of the reference assay devices. Then, the comparator circuit generates a comparison signal in response thereto.

The signal processor receives this comparison signal from the comparator circuit and in response thereto generates a determination signal indicative of the presence, absence or quantity of an analyte in the fluid sample tested by the assay device read by the instrument.

In an alternative embodiment of the present invention, the optics module of the instrument may include at least one light source and a light detector. The at least one light source emits light and is positioned on the instrument to direct the light onto the detection zone of the assay device placed in optical proximity to the instrument. The light detector receives reflected or fluoresced light emanating from the detection zone of the assay device in response to the light directed thereon by the at least one light source. The light detector generates an output signal in response to the reflected or fluoresced light received by the light detector, the output signal being indicative of a colorimetric change in the detection zone of the assay device. This output signal is provided to the signal processor of the instrument.

As stated previously, a method for reading a lateral flow assay device by detecting color changes thereto based on human perception is also disclosed. The method includes the steps of placing the assay device in optical proximity to an assay reader, such as described previously, such that the detection zone of the assay device is viewable by the at least one camera of the assay reader. The method further includes the step of generating an output signal by the at least one camera, which output signal is representative of an image of the detection zone of the assay device and which is indicative of a colorimetric change in the detection zone of the assay device.

Then, in accordance with the method of the present invention, the output signal from the at least one camera is received by the signal processor of the assay reader. The method then includes the step of converting the output signal from the at least one camera by the signal processor into measured colorimetric data. The comparator circuit of the assay reader then compares the measured colorimetric data relating to the assay device read by the assay reader with the dataset of sample readings based on human visual perceptions of the colorimetric changes of the reference assay devices stored in the storage memory of the assay reader.

In further accordance with the method of the present invention, the comparator circuit generates a comparison signal in response to comparing the measured colorimetric data with the stored dataset. The comparison signal from the comparator circuit is received by the signal processor, and, in accordance with the method, the signal processor generates a determination signal in response to the received comparison signal indicative of the presence, absence or quantity of an analyte in the fluid sample tested by the assay device read by the assay reader.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Figure 1:
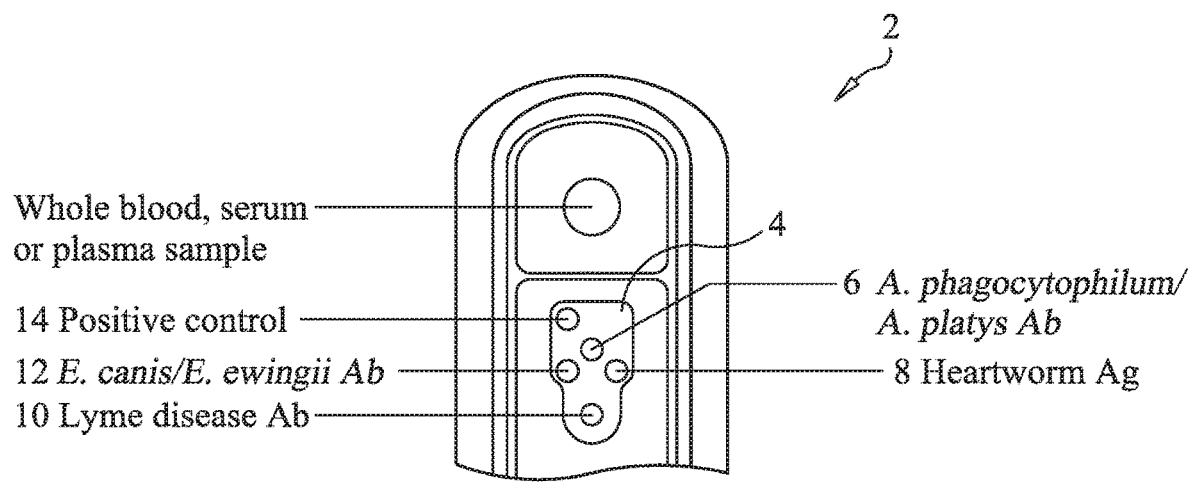
FIG. 1 is a front view of a portion of a lateral flow assay device and, in particular, a SNAP® assay device manufactured by IDEXX Laboratories, Inc., and showing the read area on the device and several detection zones forming part of the read area.
Figure 2:
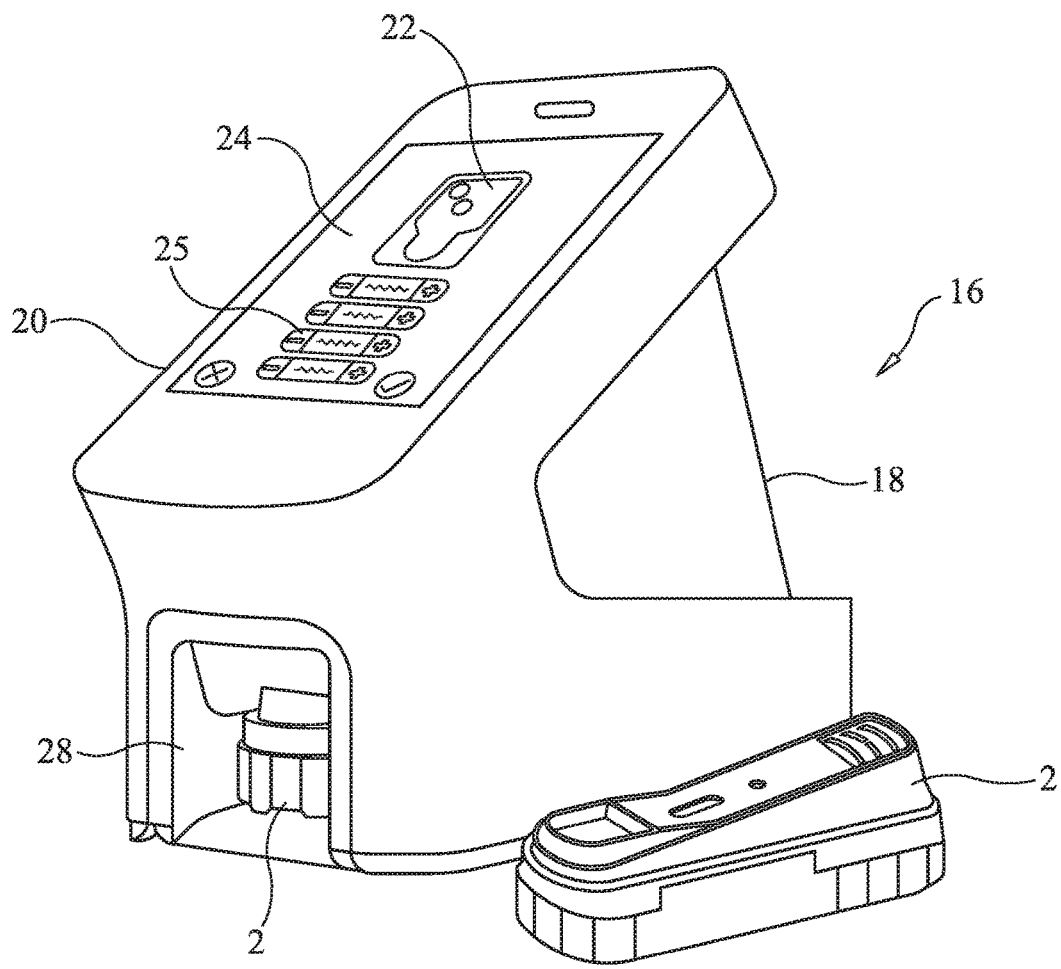
FIG. 2 is a perspective view of a SNAP® lateral flow assay device and a reader formed in accordance with the present invention.

Reference should initially be had to FIG. 2 of the drawings. There, a SNAP® lateral flow assay device 2 is shown adjacent to the reader 16 for the device 2 constructed in accordance with the present invention. It should be realized, of course, that the reader 16 of the present invention disclosed herein is not limited to use solely with a SNAP® assay device 2, and that the structure of the reader 16 and method disclosed herein may be used with many different types of lateral flow assay devices 2 on the market, including reversible (bi-directional) flow chromatographic binding assay devices, uni-directional lateral flow assay devices and lateral flow assay devices having colloidal gold particles.

As shown in FIG. 2 of the drawings, the reader 16 of the present invention includes a housing 18 which is preferably in the form of a rectangular parallelepiped having a sloping top surface 20 on which is situated a display 22 and a graphical user interface (GUI) 24 having switches or a keyboard 25 and indicators for inputting data and commands and for receiving information concerning the tests being performed on a lateral flow assay device 2, such as the SNAP® device. The display 22 is preferably a liquid crystal display (LCD), which effectively provides an indication of what is displayed in the read area 4 of the assay device 2, including a display of the detection zones 6, 8, 10, 12 and the control portion 14 of the read area 4. The display 22 effectively recreates what is shown on the read area 4 of the lateral flow assay device 2 being tested, which is viewed by the camera 26 of the reader 16 in optical communication with the read area 4 of the assay device 2. The housing 18 includes an opening or a port 28 on one side thereof to closely receive a lateral flow assay device 2, such as the SNAP® device. When received by the port 28, the lateral flow assay device 2 is maintained in a position such that the camera 26 of the reader 16 is in optical alignment with the detection zones 6, 8, 10, 12 of the read area 4 on the assay device 2.

Figure 3:
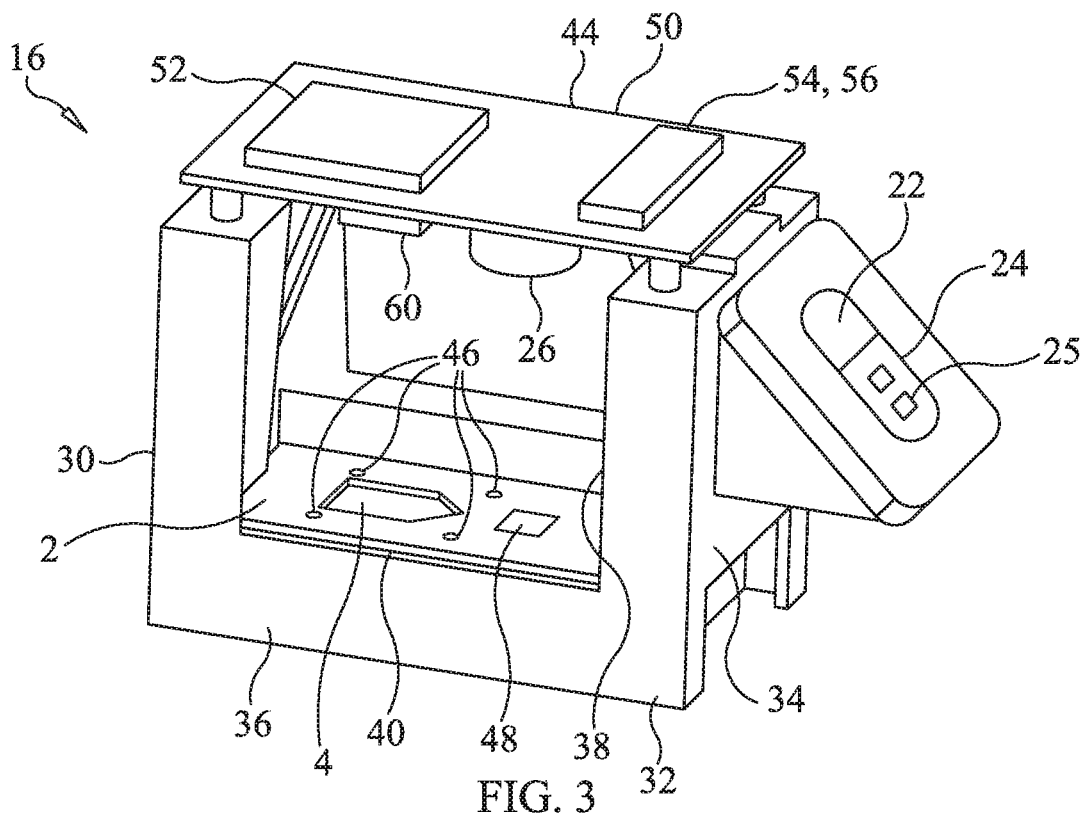
FIG. 3 is a top, side perspective view of a lateral flow assay device reader formed in accordance with another form of the present invention.
Figure 4:
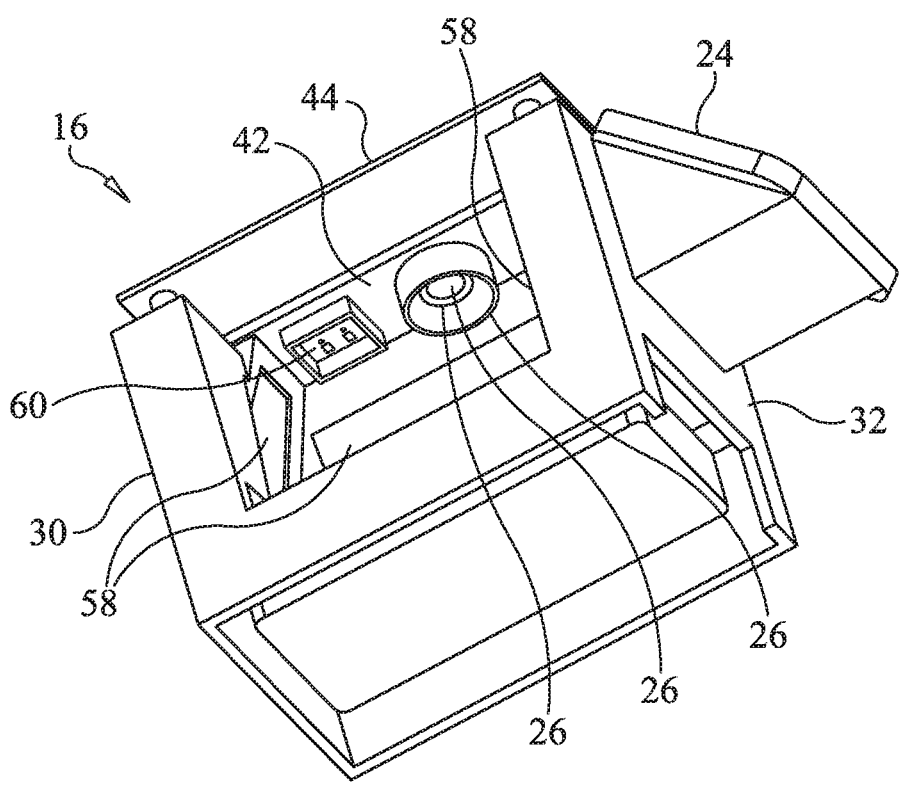
FIG. 4 is a bottom, side perspective view of the lateral flow assay device reader of the present invention shown in FIG. 3.
Figure 5:
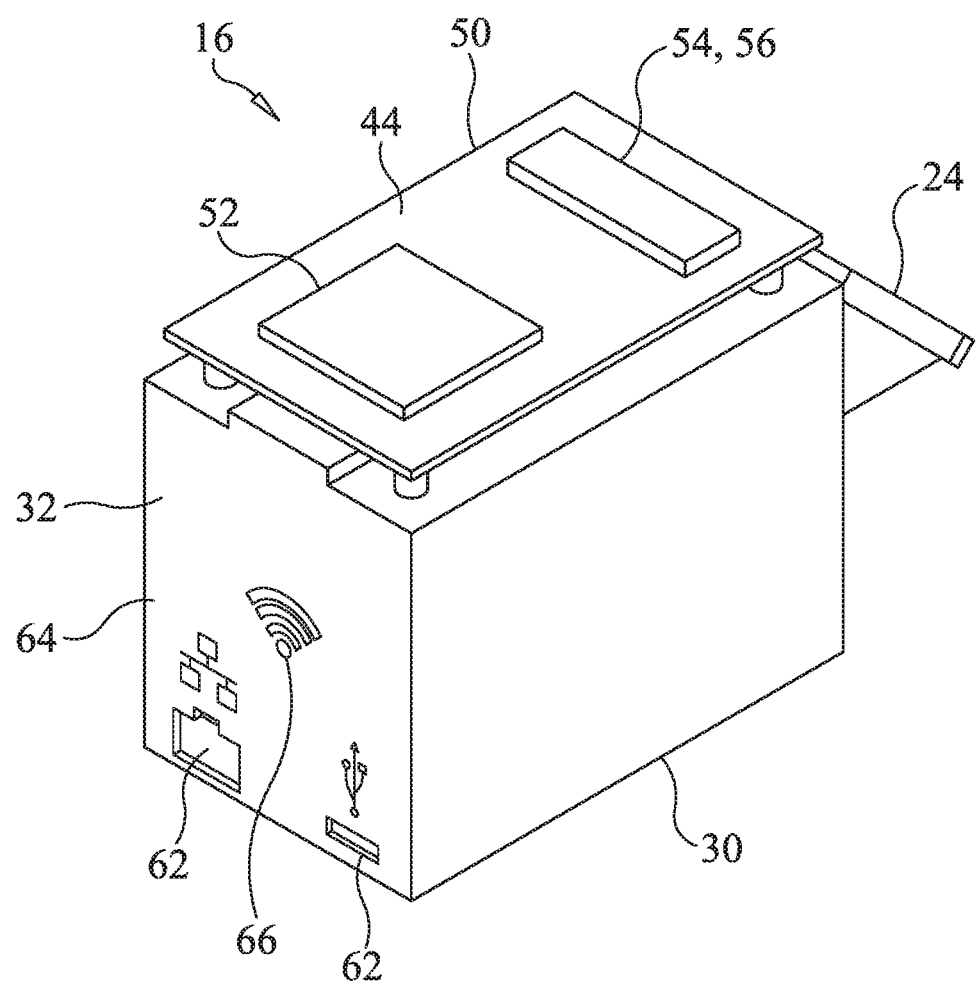
FIG. 5 is a top, rear perspective view of the lateral flow assay device reader of the present invention shown in FIGS. 3 and 4.

Another form of the lateral flow assay device reader 16 of the present invention is shown in FIGS. 3-5. These figures show a simplistic view of the assay reader 16, with the outer housing removed therefrom, to facilitate an understanding of some of the major components of the reader 16.

More specifically, and referring to FIGS. 3-5 of the drawings, it can be seen that the lateral flow assay device reader 16 of the present invention is, like the reader 16 shown in FIG. 2, formed generally in the shape of a rectangular parallelepiped. The reader 16 has an internal frame 30 having sidewalls 32, and a graphical user interface (GUI) 24 is preferably mounted on one of the sidewalls of the frame, such as the front sidewall 34. The GUI 24 is preferably sloped with respect to the sidewall 34 of the frame 30 on which it is mounted so that a display 22 of the GUI 24 and any switches or keyboard 25, or other indicators, may be easily viewed and accessed by a user of the assay reader 16.

As can be seen from FIGS. 3 and 4 of the drawings, one of the sidewalls 32 of the frame 30, such as a lateral sidewall 36, includes a cutout to form a pocket 38 having a ledge or support surface 40 on which a lateral flow assay device 2 may rest. This pocket 38 formed in the frame 30 is in alignment with an opening formed in the outer housing (not shown) of the reader 16 so that a user may have access to the pocket 38 and place an assay device 2 within the confines of the pocket 38. The assay device 2, when placed on the support surface 40 within the pocket 38, is maintained in a position such that the read area 4 or window of the assay device 2 is in optical alignment with an optics module 42, preferably a camera 26, situated above it and mounted on the underside of a printed circuit board 44 affixed to the frame 30. Preferably, the lateral flow assay device 2 includes calibration targets 46 in the form of markings or indicia which are placed in four corners surrounding the read window or area 4 of the lateral flow assay device 2. The calibration targets 46 are used to insure that the read window or area 4 of the lateral flow assay device 2 placed within the pocket 38 of the reader 16 is in proper optical alignment with the optics module 42 of the reader 16. Preferably, the lateral flow assay device 2 further includes a bar code 48 or other indicia to identify the type of assay device 2 placed in the reader 16, such as the SNAP® 4Dx® Plus assay device, the SNAP® Heartworm RT assay device, the SNAP® Feline Triple® assay device, the SNAP® FIV/FeLV Combo assay device, the SNAP® *Parvo* assay device, the SNAP® *Giardia* assay device, the SNAP® Lepto assay device, the SNAP® cPL™ assay device, the SNAP® fPL™ assay device and the SNAP® Feline proBNP assay device, each of which is manufactured or distributed by IDEXX Laboratories, Inc. Clearly, other lateral flow device manufacturers can incorporate bar codes on their respective devices for proper identification.

The printed circuit board 44 referred to herein generally includes the circuitry that comprises the signal processing unit 50 of the reader 16. The signal processing unit 50 includes a central processing unit (CPU) 52, which carries out the operation of the reader 16 and its various functions, and various memories, including a random access memory (RAM) 54 and a read only memory (ROM) 56, as will be explained in greater detail. Some operational software is embedded in the RAM 54 and test data is also stored therein, and the ROM 56 includes a database or dataset of sample readings of reference assay devices similar in structure and function to that of the assay device 2 read by the assay reader 16. The sample readings are based on human visual perceptions of colorimetric changes in the detection zones of the reference assay devices.

The internal cavity, or pocket 38, of the frame 30 of the assay reader 16 may include one or more diffuse reflectors 58 mounted on the internal surfaces of the sidewalls 32 thereof to insure that any light illuminating the lateral flow assay device 2 and emitted by one or more light emitting devices, such as light emitting diodes (LEDs), or other structured lighting 60, is directed onto the read window or area 4 of the lateral flow assay device 2 situated within the pocket 38 of the assay reader 16. The LED lighting 60 is preferably mounted on the underside of the printed circuit board 44 to direct light downwardly onto the lateral flow assay device 2. The optics module 42 is also mounted on the underside of the printed circuit board 44 and situated above the pocket 38 and a lateral flow assay device 2 received therein, and may include one or more cameras 26, as mentioned previously.

As can be seen from FIG. 5 of the drawings, the assay reader 16 may include connectors or ports 62 for Ethernet or internet connections to external equipment. In the case of IDEXX Laboratories, Inc, this could include connection to the IDEXX VetLab® Station which is capable of communicating with other instruments, such as the VetTest™, Catalyst DX™, Catalyst One™ and SediVue Dx™ analyzers manufactured or distributed by IDEXX Laboratories, Inc. These connectors 62 are preferably mounted on a rear sidewall 64 of the frame 30, or the outer housing, of the assay reader 16. Furthermore, the assay reader 16 includes a speaker or transducer 66, also mounted on the rear sidewall 64 or another sidewall 32 of either the outer housing or the internal frame 30 of the assay reader 18, to convey audible information to the user of the assay reader 16. The speaker, or transducer 66, and the Ethernet and internet ports 62 are electrically connected to the signal processing unit 50 of the assay reader 16.

Figure 6:
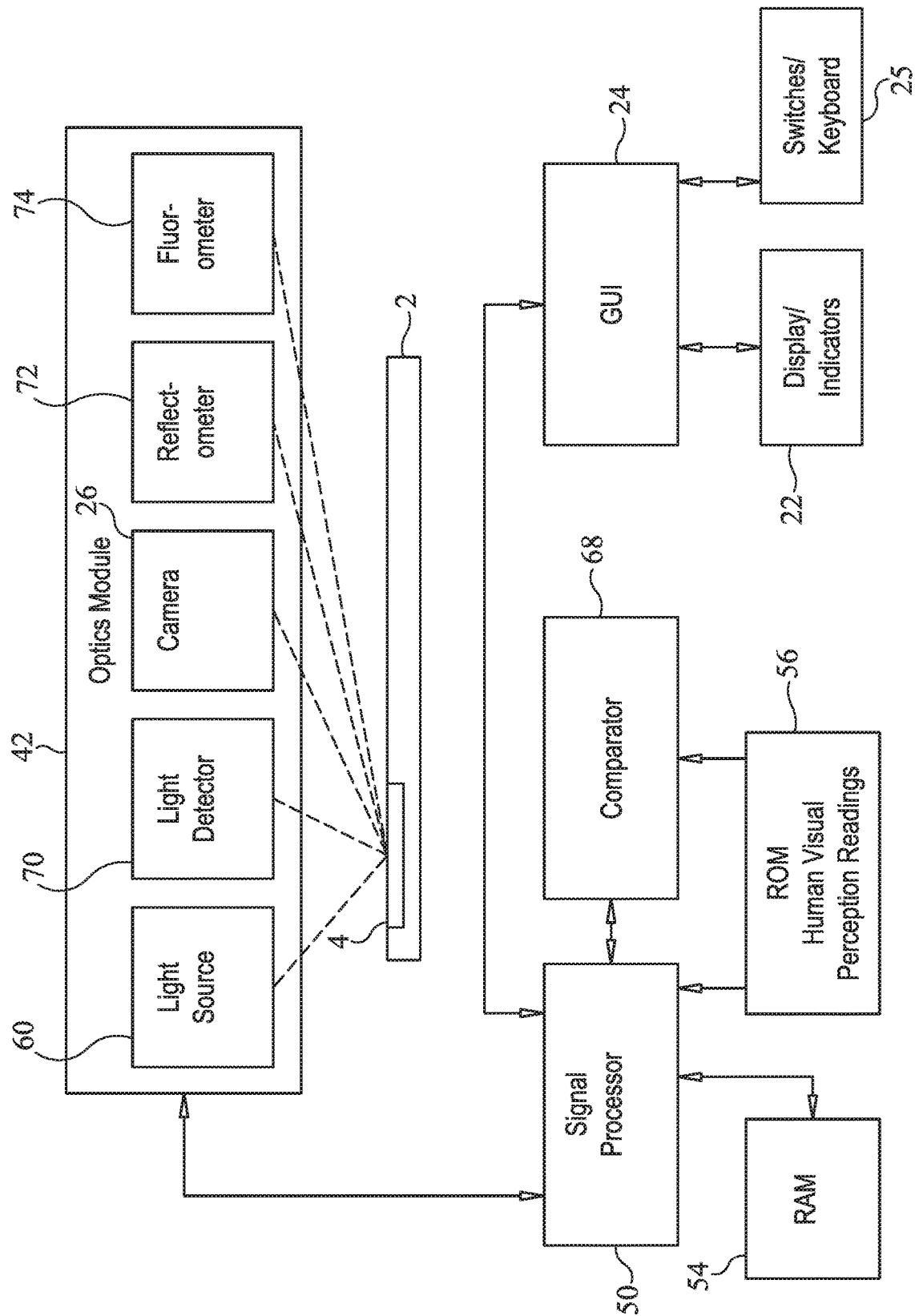
FIG. 6 is a block diagram of the optical and electronic components of the lateral flow assay device reader of the present invention.

FIG. 6 shows a block diagram of some of the electrical and optical components of the assay reader 16 of the present invention. As can be seen from FIG. 6, the assay reader 16 preferably includes an optics module 42, as mentioned previously. The optics module 42 preferably has at least one camera 26 that is positioned on the reader 16 to view the detection zones 6, 8, 10, 12 (e.g., the "dots" mentioned earlier) in the read area 4 of the assay device 2 placed in optical proximity to the instrument. The at least one camera 26 generates an output signal which is representative of an image of the read area 4 and detection zones 6, 8, 10, 12 of the assay device 2 and which is indicative of a colorimetric change in the detection zones 6, 8, 10, 12 of the assay device 2. Detection zones are not limited to "dots" but can include lines or other shapes where a capture reagent is disposed on the matrix upon which the sample flows.

As also mentioned previously, there is a signal processor 50 forming part of the assay reader 16. This signal processor 50 is in electrical communication with the optics module 42. The signal processor 50 receives the output signal from the at least one camera 26 and converts the signal into measured colorimetric data.

The assay reader 16 further includes a storage memory (such as the ROM 56 mentioned earlier) that is in electrical communication with the signal processor 50. The storage memory 56 has stored therein a dataset of sample readings of reference assay devices that are similar in structure and function to that of the assay device 2 read by the instrument 16. The sample readings are based on human visual perceptions of colorimetric changes in the detection zones of the reference assay devices.

The assay reader 16 further includes a comparator circuit 68 which is in electrical communication with the signal processor 50 and which may form part of the signal processor 50. The comparator circuit 68 compares the measured colorimetric data relating to the assay device 2 read by the instrument 16 with the stored dataset or database of sample readings based on human visual perceptions of the colorimetric changes of the reference assay devices, and generates a comparison signal in response thereto. The signal processor 50 receives the comparison signal from the comparator circuit 68, and in response thereto, generates a determination signal that is indicative of the presence, absence or quantity of an analyte (e.g., an antigen or an antibody) in the fluid sample tested by the assay device 2 read by the instrument 16.

As mentioned previously, the optics module 42 may include at least one camera 26. However, in an alternative embodiment of the present invention, the optics module 42 of the assay reader 16 may include at least one light source 60 and a light detector 70. The light source 60 and light detector 70 may be formed, for example, as a reflectometer 72 or a fluorometer 74. The at least one light source 60 emits light and is positioned on the assay reader 16, such as on the underside of the overhead printed circuit board 44, to direct the light onto the detection zones 6, 8, 10, 12 of the read window 4 of the assay device 2 placed in optical proximity to the reader 16. The light detector 70 receives reflected or fluoresced light emanating from the detection zones 6, 8, 10, 12 of the assay device 2 in response to the light directed thereon by the at least one light source 60. The light detector 70 generates an output signal in response to the reflected or fluoresced light received by the light detector 70. The output signal from the light detector 70 is indicative of a colorimetric change in the detection zones 6, 8, 10, 12 of the assay device 2. This output signal is provided to the signal processor 50 of the assay reader 16.

One of the important distinguishing features of the assay reader 16 of the present invention over other instruments used to read lateral flow assay devices 2 is that the assay reader 16 "mimics" what a human would do when perceiving whether there is a color change in the detection zone or zones 6, 8, 10, 12 of the lateral flow assay device 2. In other words, the assay reader 16 of the present invention bases the determination of whether there is a colorimetric change in the detection zone 6, 8, 10, 12 of the lateral flow assay device 2 that is indicative of the presence, absence or quantity of an analyte in the fluid sample tested by the assay device 2 and read by the assay reader 16 based on human visual perception, and not based on an algorithmic rule which makes such determinations in conventional lateral flow assay device readers. The dataset or database of sample readings of reference assay devices of similar function and structure to that of the assay device 2 read by the assay reader 16 is, basically, a library of human visual calls (i.e., determinations) to images from which their observations were made. More specifically, in a specific embodiment, this stored library of human visual observations preferably includes about 4 million, or more, sample readings, or observations, made by humans of similar lateral flow assay devices. For example, if a number of manual or human reads of images of lateral flow assay devices in the dataset stored in the memory 56 reflect a positive, or negative, determination of crescent-shaped blue detection dots, or speckles instead of a full circular dot, or a light colored detection dot, then the comparator circuit 68 of the assay reader 16, and the signal processor 50 in electrical communication therewith, will make a similar determination, based on the stored dataset of sample readings of human visual perceptions of the colorimetric changes of the reference assay devices. From this, the assay reader 16 of the present invention, and in particular, the signal processor 50 thereof, generates a determination signal that is indicative of the presence or quantity, or absence, of an analyte in the fluid sample tested by the assay device 2 read by the assay reader 16.

As further mentioned previously, a method for reading a lateral flow assay device 2 by detecting color changes thereto based on human perception is also disclosed herein. The method is performed by a lateral flow assay reader 16, which preferably has an optics module 42, a signal processor 50 in electrical communication with the optics module 42, a storage memory 56 in electrical communication with the signal processor 50 and a comparator circuit 68 in electrical communication with the signal processor 50. The optics module 42 has at least one camera 26. The storage memory 56 has stored therein a dataset of sample readings of reference assay devices similar in structure and function to that of the assay device 2 read by the assay reader 16. The sample readings of the dataset are based on human visual perceptions of colorimetric changes in the detection zones of the reference assay devices.

The method includes the step of placing the lateral flow assay device 2 in optical proximity to the assay reader 16 such that the detection zone 6, 8, 10, 12 of the assay device 2 is viewable by the at least one camera 26 of the assay reader 16. Then, the method includes the step of generating an output signal by the at least one camera 26 which is representative of an image of the detection zone 6, 8, 10, 12 of the assay device 2 and which is indicative of a colorimetric change in the detection zone 6, 8, 10, 12 of the assay device 2. The method further includes the steps of receiving by the signal processor 50 of the assay reader 16 the output signal from the at least one camera 26, and converting by the signal processor 50 the output signal from the at least one camera 26 into measured colorimetric data. This measured colorimetric data is preferably stored in the RAM 54.

The method of the present invention further compares, using the comparator circuit 68 of the assay reader 16, the measured colorimetric data relating to the assay device 2 read by the assay reader 16 with the dataset of sample readings based on human visual perceptions of the colorimetric changes of the reference assay devices stored in the storage memory 56 of the assay device reader 16. Then, the method includes the steps of generating by the comparator circuit 68 a comparison signal in response to comparing the measured colorimetric data with the stored dataset, receiving by the signal processor 50 the comparison signal from the comparator circuit 68, and generating by the signal processor 50 a determination signal in response to the received comparison signal indicative of the presence, absence or quantity of an analyte in the fluid sample tested by the assay device 2 read by the assay reader 16.

The at least one camera 26 of the assay reader 16 may be a charge-coupled device (CCD). However, and as mentioned previously, the optics module 42 may use at least one light source 60, and a light detector 70 instead of the camera 26. Then, the method of the present invention would include the steps of directing light from the at least one light source 60 of the optics module 42 of the assay reader 16 onto the detection zone 6, 8, 10, 12 of the assay device 16, receiving by the light detector 70 of the optics module 42 of the assay reader 16 reflected or fluoresced light emanating from the detection zone 6, 8, 10, 12 of the assay device 2 in response to the light directed thereon by the at least one light source 60, and generating by the light detector 70 an output signal in response to the received reflected or fluoresced light, the output signal being indicative of a colorimetric change in the detection zone 6, 8, 10, 12 of the assay device 2. This output signal from the light detector 70 is provided to the signal processor 50 of the assay reader 16 and is converted by the signal processor 50 into measured colorimetric data.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An instrument for reading an assay device placed in optical proximity thereto for performing an assay to determine the presence, absence or quantity of an analyte in a fluid sample, the assay device having a sample deposit zone on which a fluid sample to be tested is placed and further having a detection zone in which a visually perceptible colorimetric change may occur when the assay device detects the presence, absence or quantity of an analyte in the fluid sample, the instrument comprising:
   an optics module, the optics module having at least one light source and a light detector, the at least one light source emitting light and being positioned on the instrument to direct the light onto the detection zone of the assay device placed in optical proximity to the instrument, the light detector receiving reflected or fluoresced light emanating from the detection zone of the assay device in response to the light directed thereon by the at least one light source, and generating an output signal in response to the reflected or fluoresced light received by the light detector, the output signal being indicative of a colorimetric change in the detection zone of the assay device;
   a signal processor in electrical communication with the optics module, the signal processor receiving the output signal from the light detector and converting the signal into measured colorimetric data;
   a memory in electrical communication with the signal processor; and
   a comparator circuit in electrical communication with the signal processor, the comparator circuit comparing the measured colorimetric data relating to the assay device read by the instrument with a dataset of sample readings of reference assay devices similar in structure and function to that of the assay device read by the instrument, the sample readings being based on human visual perceptions of colorimetric changes in the detection zones of the reference assay devices, and generating a comparison signal in response thereto, the signal processor receiving the comparison signal from the comparator circuit and in response thereto generating a determination signal indicative of the presence, absence of quantity of an analyte in the fluid sample tested by the assay device read by the instrument.

2. An instrument as defined by claim 1, which further comprises:
   a housing, the housing having side walls defining an interior cavity, the optics module, signal processor, memory and comparator circuit being situated within the interior cavity.

3. An instrument as defined by claim 2, wherein one of the side walls of the housing has formed therein a receptacle for at least partially receiving therein the assay device read by the instrument, the at least one light source and the light detector of the optics module being in optical communication with the receptacle and an assay device received thereby.

4. An instrument as defined by claim 1, which further comprises:
   a main housing, the main housing having side walls defining an interior cavity;
   wherein the optics module is situated within the interior cavity of the main housing; and
   wherein the signal processor, memory and comparator circuit are situated in a remote location from the main housing of the instrument.

5. An instrument as defined by claim 1, which further comprises:
   a main housing, the main housing having side walls defining an interior cavity;
   wherein the optics module is situated within the interior cavity of the main housing; and
   wherein the dataset of sample readings based on human visual perceptions of the colorimetric changes of the reference assay devices is stored at a remote location from the main housing of the instrument.

6. The instrument of claim 1, wherein the assay device is a reversible flow chromatographic binding assay device.

7. The instrument of claim 1, wherein the assay device comprises colloidal gold particles.

8. In combination:
   an assay device for performing an assay to determine the presence, absence or quantity of an analyte in a fluid sample, the assay device having a sample deposit zone on which a fluid sample to be tested is placed and further having a detection zone in which a visually perceptible colorimetric change may occur when the assay device detects the presence, absence or quantity of an analyte in the fluid sample; and an assay reader which detects color changes based on human perception, the assay device being placed in optical proximity to the assay reader, the assay reader including:

an optics module, the optics module having at least one light source and a light detector, the at least one light source emitting light and being positioned with respect to the assay device to direct the light emitted thereby onto the detection zone of the assay device, the light detector receiving reflected or fluoresced light emanating from the detection zone of the assay device in response to the light directed thereon by the at least one light source, and generating an output signal in response to the reflected or fluoresced light received by the light detector, the output signal being indicative of a colorimetric change in the detection zone of the assay device;

a signal processor in communication with the optics module, the signal processor receiving the output signal from the light detector and converting the signal into measured colorimetric data;

a memory in electrical communication with the signal processor; and a comparator circuit in electrical communication with the signal processor, the comparator circuit comparing the measured colorimetric data relating to the assay device read by the assay reader with a dataset of sample readings of reference assay devices similar in structure and function to that of the assay device read by the assay reader, the sample readings being based on human visual perceptions of colorimetric changes in the detection zones of the reference assay devices, and generating a comparison signal in response thereto, the signal processor receiving the comparison signal from the comparator circuit and in response thereto generating a determination signal indicative of the presence, absence or quantity of an analyte in the fluid sample tested by the assay device read by the assay reader.

9. A combination as defined by claim 8, wherein the assay reader further includes a housing, the housing having side walls defining an interior cavity, the optics module, signal processor, memory and comparator circuit being situated within the interior cavity.

10. A combination as defined by claim 9, wherein one of the side walls of the housing of the assay reader has formed therein a receptacle for at least partially receiving therein the assay device read by the assay reader, the at least one light source and the light detector of the optics module being in optical communication with the receptacle and an assay device received thereby.

11. A combination as defined by claim 8, wherein the assay reader further includes a main housing, the main housing having side walls defining an interior cavity;

wherein the optics module is situated within the interior cavity of the main housing; and wherein the signal processor, memory and comparator circuit are situated in a remote location from the main housing of the assay reader.

12. A combination as defined by claim 8, wherein the assay reader further includes a main housing, the main housing having side walls defining an interior cavity;

wherein the optics module is situated within the interior cavity of the main housing; and wherein the dataset of sample readings based on human visual perceptions of the colorimetric changes of the reference assay devices is stored at a remote location from the main housing of the assay reader.

13. The combination of claim 8, wherein the assay device is a reversible flow chromatographic binding assay device.

14. The combination of claim 8, wherein the assay device comprises colloidal gold particles.

15. An instrument for reading an assay device placed in optical proximity thereto for performing an assay to determine the presence, absence or quantity of an analyte in a fluid sample, the assay device having a sample deposit zone on which a fluid sample to be tested is placed and further having a detection zone in which a visually perceptible colorimetric change may occur when the assay device detects the presence, absence or quantity of an analyte in the fluid sample, the instrument comprising:

an optics module, the optics module having at least one camera, the at least one camera being positioned on the instrument to view the detection zone of the assay device placed in optical proximity to the instrument, the at least one camera generating an output signal which is representative of an image of the detection zone of the assay device and which is indicative of a colorimetric change in the detection zone of the assay device;

a signal processor in electrical communication with the optics module, the signal processor receiving the output signal from the at least one camera and converting the signal into measured colorimetric data;

a memory in electrical communication with the signal processor; and a comparator circuit in electrical communication with the signal processor, the comparator circuit comparing the measured colorimetric data relating to the assay device read by the instrument with a dataset of sample readings of reference assay devices similar in structure and function to that of the assay device read by the instrument, the sample readings being based on human visual perceptions of colorimetric changes in the detection zones of the reference assay devices, and generating a comparison signal in response thereto, the signal processor receiving the comparison signal from the comparator circuit and in response thereto generating a determination signal indicative of the presence, absence of quantity of an analyte in the fluid sample tested by the assay device read by the instrument.

16. An instrument as defined by claim 15, wherein the at least one camera is a charge-coupled device (CCD).

17. An instrument as defined by claim 15, which further comprises:

a housing, the housing having side walls defining an interior cavity, the optics module, signal processor, memory and comparator circuit being situated within the interior cavity.

18. An instrument as defined by claim 17, wherein one of the side walls of the housing has formed therein a receptacle for at least partially receiving therein the assay device read by the instrument, the at least one camera of the optics module being in optical communication with the receptacle and an assay device received thereby.

19. An instrument as defined by claim 15, which further comprises:
a main housing, the main housing having side walls defining an interior cavity;
wherein the optics module is situated within the interior cavity of the main housing; and
wherein the signal processor, memory and comparator circuit are situated in a remote location from the main housing of the instrument.

20. An instrument as defined by claim 15, which further comprises:
a main housing, the main housing having side walls defining an interior cavity;
wherein the optics module is situated within the interior cavity of the main housing; and
wherein the dataset of sample readings based on human visual perceptions of the colorimetric changes of the reference assay devices is stored at a remote location from the main housing of the instrument.

21. The instrument of claim 15, wherein the assay device is a reversible flow chromatographic binding assay device.

22. The instrument of claim 15, wherein the assay device comprises colloidal gold particles.

23. In combination:
an assay device for performing an assay to determine the presence, absence or quantity of an analyte in a fluid sample, the assay device having a sample deposit zone on which a fluid sample to be tested is placed and further having a detection zone in which a visually perceptible colorimetric change may occur when the assay device detects the presence, absence or quantity of an analyte in the fluid sample; and
an assay reader which detects color changes based on human perception, the assay device being placed in optical proximity to the assay reader, the assay reader including:
an optics module, the optics module having at least one camera, the at least one camera being positioned with respect to the assay device to view the detection zone of the assay device, the at least one camera generating an output signal which is representative of an image of the detection zone of the assay device and which is indicative of a colorimetric change in the detection zone of the assay device;
a signal processor in communication with the optics module, the signal processor receiving the output signal from the at least one camera and converting the signal into measured colorimetric data;
a memory in electrical communication with the signal processor; and
a comparator circuit in electrical communication with the signal processor, the comparator circuit comparing the measured colorimetric data relating to the assay device read by the assay reader with a dataset of sample readings of reference assay devices similar in structure and function to that of the assay device read by the assay reader, the sample readings being based on human visual perceptions of colorimetric changes in the detection zones of the reference assay devices, and generating a comparison signal in response thereto, the signal processor receiving the comparison signal from the comparator circuit and in response thereto generating a determination signal indicative of the presence, absence or quantity of an analyte in the fluid sample tested by the assay device read by the assay reader.

24. A combination as defined by claim 23, wherein the at least one camera of the assay reader is a charge-coupled device (CCD).

25. A combination as defined by claim 23, wherein the assay reader further includes a housing, the housing having side walls defining an interior cavity, the optics module, signal processor, memory and comparator circuit being situated within the interior cavity.

26. A combination as defined by claim 25, wherein one of the side walls of the housing of the assay reader has formed therein a receptacle for at least partially receiving therein the assay device read by the assay reader, the at least one camera of the optics module being in optical communication with the receptacle and an assay device received thereby.

27. A combination as defined by claim 23, wherein the assay reader further includes a main housing, the main housing having side walls defining an interior cavity;
wherein the optics module is situated within the interior cavity of the main housing; and
wherein the signal processor, memory and comparator circuit are situated in a remote location from the main housing of the assay reader.

28. A combination as defined by claim 23, wherein the assay reader further includes a main housing, the main housing having side walls defining an interior cavity;
wherein the optics module is situated within the interior cavity of the main housing; and
wherein the dataset of sample readings based on human visual perceptions of the colorimetric changes of the reference assay devices is stored at a remote location from the main housing of the assay reader.

29. The combination of claim 23, wherein the assay device is a reversible flow chromatographic binding assay device.

30. The combination of claim 23, wherein the assay device comprises colloidal gold particles.

31. A method for determining the presence, absence, or quantity of an analyte in a fluid sample tested by an assay device, the method comprising:
comparing measured colorimetric data relating to an assay device with a dataset of sample readings based on human visual perceptions of colorimetric changes of reference assay devices, the dataset of sample readings stored in a storage memory of an assay reader;
generating a comparison signal in response to the comparing the measured colorimetric data with the dataset of sample readings; and
generating a determination signal in response to the comparison signal, the determination signal indicative of the presence, absence, or quantity of an analyte in a fluid sample tested by the assay device read by the assay reader.

32. The method of claim 31, further comprising:
receiving, from an optics module of the assay reader, an output signal indicative of a colorimetric change in a detection zone of the assay device; and
converting the output signal into the measured colorimetric data.

33. The method of claim 32, wherein the converting the output signal into the measured colorimetric data comprises converting the output signal via a signal processor of the assay reader.

34. The method of claim 32, wherein the optics module comprises one or more light sources and a light detector, the method further comprising:
directing light from the one or more light sources onto the detection zone of the assay device;

receiving by the light detector, reflected or fluoresced light emanating from the detection zone of the assay device in response to the light directed thereon by the one or more light sources; and generating, by the light detector, the output signal.

35. The method of claim 32, wherein the optics module comprises one or more cameras, the method further comprising generating, by the one or more cameras, the output signal, the output signal being representative of an image of the detection zone of the assay device and which is indicative of a colorimetric change in the detection zone of the assay device.

36. The method of claim 35, further comprising displaying, on a display of the assay reader, the detection zone of the assay device.

37. The method of claim 31, wherein the dataset of sample readings based on human visual perceptions reflect a positive, or negative, determination of one or more of crescent-shaped blue detection dots, or speckles instead of a full circular dot, or a light colored detection dot.

38. The method of claim 31, wherein the assay reader comprises a graphical user interface.

39. The method of claim 31, wherein the assay device is a reversible flow chromatographic binding assay device.

40. The method of claim 31, wherein the assay device comprises colloidal gold particles.

41. The method of claim 31, wherein the assay device screens for vector-borne diseases.

42. The method of claim 31, wherein the assay device comprises indicia indicative of an assay device type.

43. The method of claim 31, wherein the assay device comprises calibration targets in the form of markings or indicia.

44. An instrument for reading an assay device placed in optical proximity thereto for performing an assay to determine the presence, absence of quantity of an analyte in a fluid sample, the instrument comprising:

a housing comprising side walls defining an interior cavity;

an optics module situated within the interior cavity, the optics module comprising at least one of (1) one or more cameras, or (2) one or more light emitting sources and a light detector, the optics module generating an output signal being indicative of a colorimetric change in a detection zone of an assay device;

a signal processor in communication with the optics module, the signal processor receiving the output signal from the optics module and converting the signal into measured colorimetric data;

a storage memory in communication with the signal processor, the storage memory having stored therein a dataset of sample readings of reference assay devices similar in structure and function to that of the assay device read by the instrument, the sample readings being based on human visual perceptions of colorimetric changes in the detection zones of the reference assay devices; and a comparator circuit in communication with the signal processor, wherein the comparator circuit compares the measured colorimetric data with the dataset of sample readings.

45. The instrument of claim 44, wherein the housing defines a port to receive the assay device.

46. The instrument of claim 44, wherein the interior cavity defines a ledge on which the assay device is positionable.

47. The instrument of claim 44, further comprising a display that is configured to display an indication of what is displayed in a read area of the assay device.

48. The instrument of claim 47, wherein the display comprises a graphical user interface.

49. The instrument of claim 44, further comprising a display that is configured to display an image of a read area of the assay device.

50. The instrument of claim 49, wherein the display comprises a graphical user interface.

\* \* \* \* \*